United States Patent
Iwanaga

(10) Patent No.: US 7,235,051 B2
(45) Date of Patent: Jun. 26, 2007

(54) NONCONTACT TONOMETER

(75) Inventor: Tomoyuki Iwanaga, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 348 days.

(21) Appl. No.: 10/645,480

(22) Filed: Aug. 22, 2003

(65) Prior Publication Data

US 2004/0046936 A1 Mar. 11, 2004

(30) Foreign Application Priority Data

Sep. 11, 2002 (JP) .............................. 2002-265706

(51) Int. Cl.
*A61B 3/16* (2006.01)
(52) U.S. Cl. ..................................... 600/401
(58) Field of Classification Search ........ 600/398–405, 600/561, 587; 351/200
See application file for complete search history.

(56) References Cited

U.S. PATENT DOCUMENTS

| | | | | |
|---|---|---|---|---|
| 5,634,463 A * | 6/1997 | Hayafuji | ..................... | 600/405 |
| 5,946,073 A * | 8/1999 | Miwa | ......................... | 351/205 |
| 6,042,544 A * | 3/2000 | Miwa et al. | ................ | 600/399 |
| 6,131,574 A * | 10/2000 | Kohayakawa | ............... | 600/401 |
| 6,234,966 B1 | 5/2001 | Miwa | | |
| 6,602,192 B2 * | 8/2003 | Miwa | ......................... | 600/401 |
| 6,817,981 B2 * | 11/2004 | Luce | .......................... | 600/399 |
| 6,875,175 B2 * | 4/2005 | Luce | .......................... | 600/398 |
| 2002/0103427 A1 * | 8/2002 | Miwa et al. | ................ | 600/401 |

FOREIGN PATENT DOCUMENTS

| | | |
|---|---|---|
| CN | 2031973 Y | 12/1998 |
| EP | 1 121 895 A2 | 8/2001 |
| JP | 2-283349 | 11/1990 |
| JP | 3-85136 | 10/1991 |
| JP | 8-196511 | 6/1996 |
| JP | 9-84760 | 3/1997 |

OTHER PUBLICATIONS

US 5,033,470, 07/1991, Yano et al. (withdrawn)

* cited by examiner

*Primary Examiner*—Max F. Hindenburg
*Assistant Examiner*—Brian Szmal
(74) *Attorney, Agent, or Firm*—Fitzpatrick, Cella, Harper & Scinto

(57) ABSTRACT

A tonometer for quickly and efficiently remeasuring intraocular pressure when an intraocular pressure is higher or lower than a predetermined pressure. It is determined whether a predetermined number n of intraocular-pressure measurements have been completed, wherein when n intraocular pressures exist, the n intraocular pressures are compared with a predetermined upper limit and lower limit. When the n intraocular pressures are between the upper limit and the lower limit, it is then determined whether the measurements of left and right eyes have been completed. When the measurements have not been completed, a measuring section is moved to the other eye. When the lateral movement has been completed, the next intraocular-pressure measurement is performed. When, among the n intraocular pressures, at least one intraocular pressure outside the predetermined upper and lower limits exists, a warning is given.

12 Claims, 6 Drawing Sheets

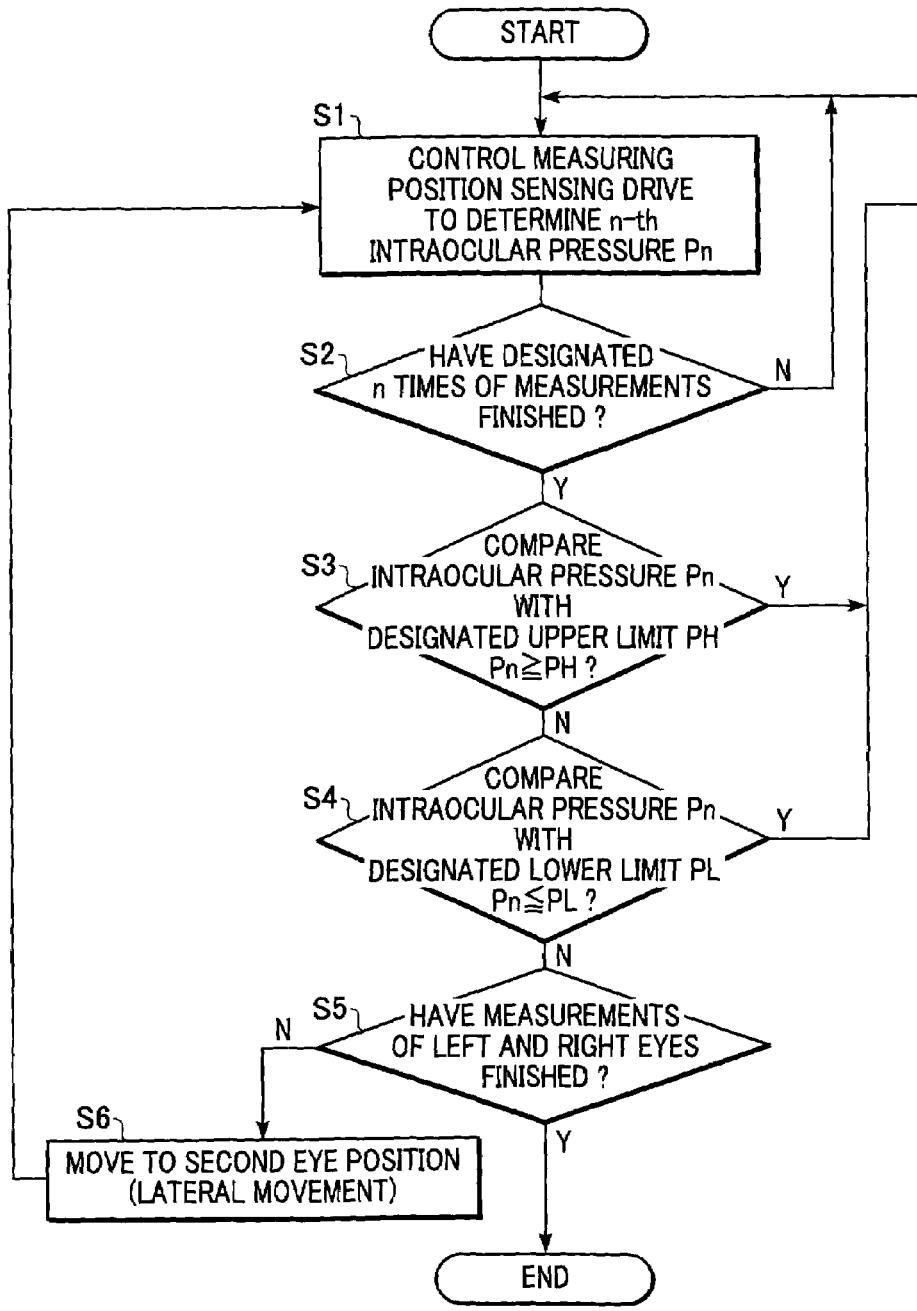

NONCONTACT TONOMETER

BACKGROUND OF THE INVENTION

1. Field of the Invention

The present invention relates to a noncontact tonometer for measuring intraocular pressure by blowing fluid such as air against the cornea of a subject eye to deform it and detecting and analyzing a change in index light projected onto the cornea.

2. Description of the Related Art

Noncontact tonometers have the advantages of no eye contact and requiring no eye-drop anesthetic and so on, thus being broadly used in the field of ophthalmology for screening to detect glaucoma caused by high intraocular pressure. When intraocular pressure is more than a predetermined value, close examinations including an eyeground examination and campimetry are performed.

An automatic positioning system is disclosed in Japanese Patent Laid-Open No. 9-84760 assigned to the same assignee as this application, in which an index image projected on a subject eye is sensed to determine the relative position between the eye and a measuring section, and a stage is controlled by motor drive.

Also, noncontact tonometers capable of full automatic measurement are going into practical use in which upon completion of predetermined times of measurements, the measuring section moves automatically to the other eye that has not yet been measured to position it and makes a predetermined number of measurements.

With the related-art noncontact tonometers, however, if eyelashes are caught on the cornea during the measurement, the resistance of the eyelashes prevents the cornea from being sufficiently deformed, so that even when the actual intraocular pressure is within a normal range, the reading sometimes indicates a higher value. Also when the fixation of the subject eye is out of place, the reading shows a lower value than the actual intraocular pressure, but only rarely. Therefore, when the intraocular pressure is higher or lower than a predetermined value, examiners perform remeasurement for confirmation.

In a case with a fully automatic system in which a measuring position is sensed, positioned automatically, and a predetermined number of measurements are sequentially performed for both eyes, when a predetermined number of measurements for one eye have been completed, the measuring section is moved to the other eye that has not yet been measured and performs a predetermined number of measurements. Therefore, the measuring section must be moved again if remeasurement for the first subject eye is necessary, thus preventing the reduction in the time required for measurements. Also, since the measuring operation has been completed, the measurement for confirmation is sometimes forgotten.

SUMMARY OF THE INVENTION

The present invention can provide a noncontact tonometer capable of solving the above-described problems to quickly and efficiently perform remeasurement for confirmation when intraocular pressure is higher or lower than a predetermined value.

The present invention proposes a noncontact tonometer characterized in that a predetermined intraocular pressure and a measured intraocular pressure are compared in magnitude and a measuring operation is varied depending on the comparison.

Further objects, features and advantages of the present invention will become apparent from the following description of the preferred embodiments (with reference to the attached drawings).

DESCRIPTION OF THE PREFERRED EMBODIMENTS

The present invention will be specifically described with reference to the illustrated embodiments.

First Embodiment

Figure 1:
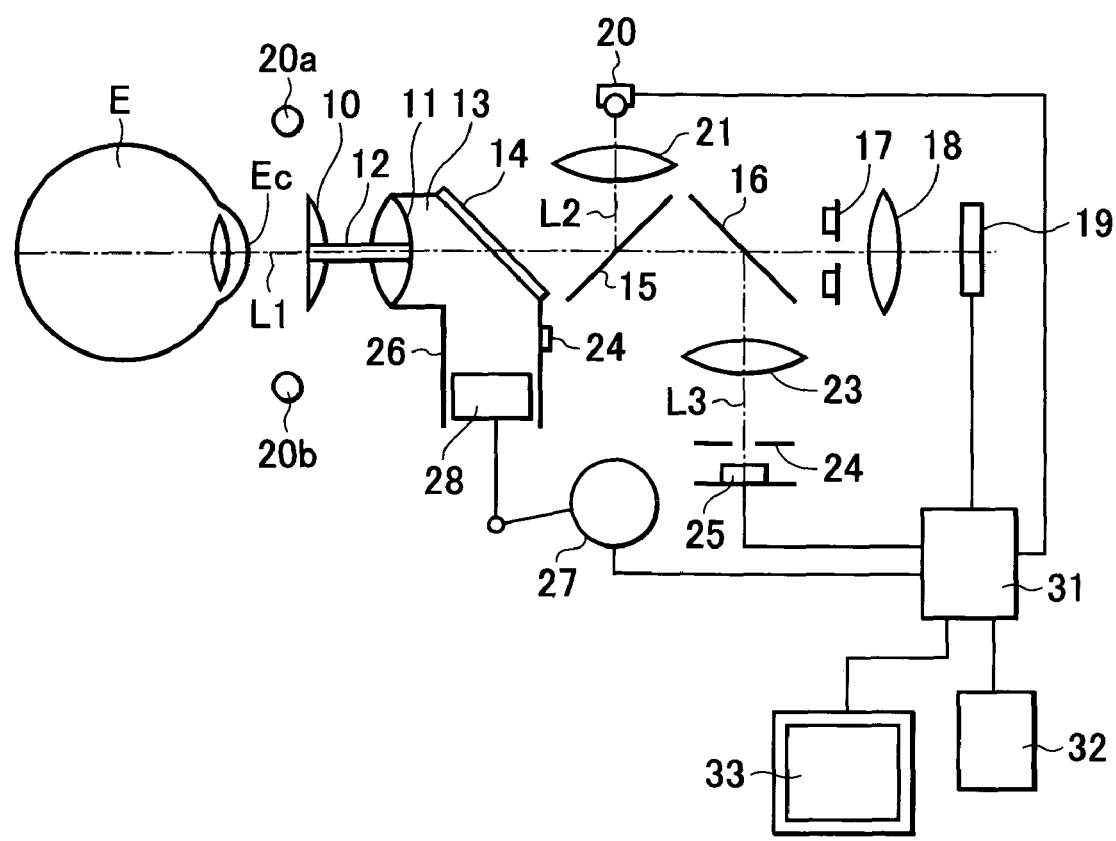
FIG. 1 is a block diagram of a first embodiment of the present invention.

FIG. 1 shows the arrangement of a measuring section of a noncontact tonometer; objective lenses 10 and 11 are disposed on an optical axis L1, facing a subject eye E, and a nozzle 12 is disposed on the central axis thereof. A fluid chamber 13, an observing window 14, dichroic mirrors 15 and 16, a prism diaphragm 17, an imaging lens 18, and an image-pickup element 19 are arranged in line on the back of the nozzle 12.

The elements including the objective lens 10 through the image-pickup element 19 make up an observation system and an alignment check system for the subject eye E. External eye-illuminating light sources 20a and 20b are disposed in the positions symmetrical with respect to the optical axis of the objective lenses 10 and 11, for illuminating an anterior ocular segment.

The dichroic mirror 16 has a characteristic of allowing light with a wavelength of light emitted from the external eye-illuminating light sources 20a and 20b to pass through and reflecting light, except part, with a wavelength of light from an LED light source 21 for measurement and alignment, which will be described later.

Figure 2:
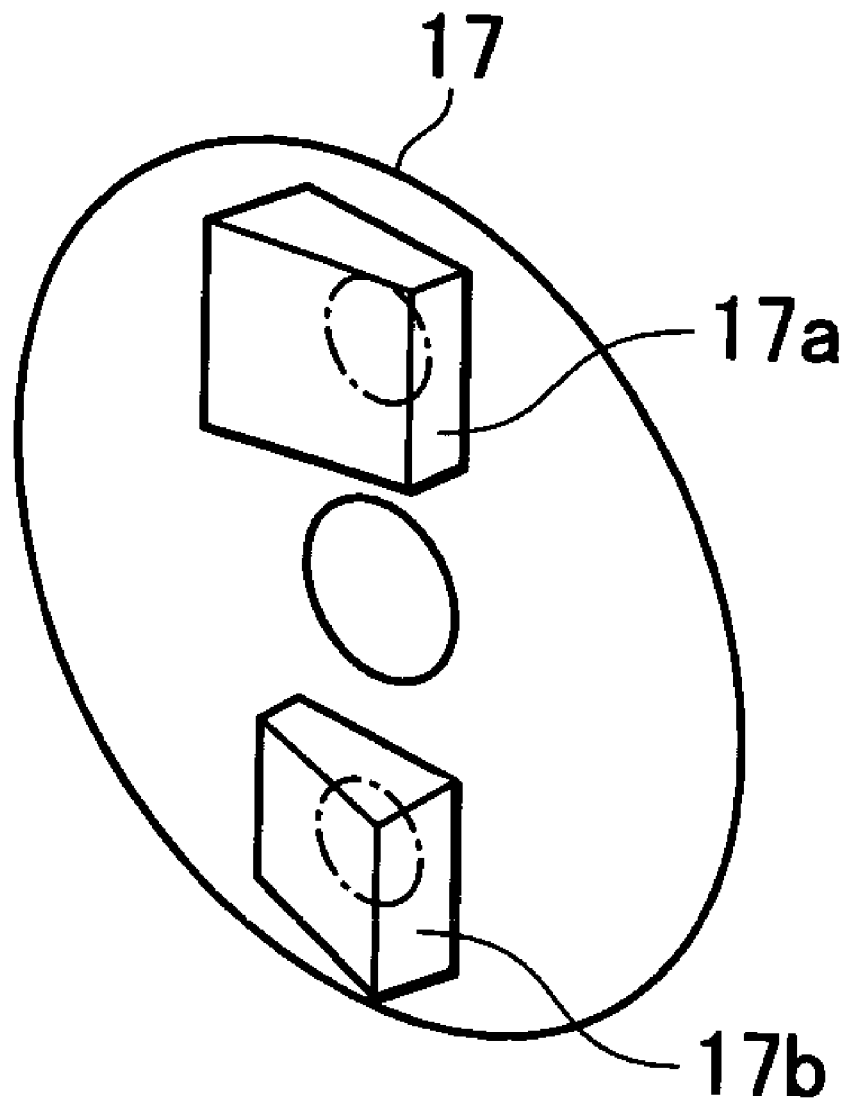
FIG. 2 is a perspective view of a prism diaphragm.

The prism diaphragm 17 has three apertures, as shown in FIG. 2. The upper and lower apertures have prisms 17a and 17b for polarizing light flux to the right and left different from each other, respectively, and also a filter having a spectral characteristic to absorb light with a wavelength of light from the external eye-illuminating light sources 20a and 20b and transmit light with a wavelength of light from the LED light source 21 for measurement and alignment.

On the other hand, the LED light source 21 for measurement and alignment and a projection lens 22 are disposed on an optical axis L2 along the reflecting direction of the dichroic mirror 15, making up a measuring-light projection system and an alignment-index projection system. Furthermore, a dichroic mirror (not shown) having the characteristic of reflecting visible light and transmitting infrared light is disposed at 45 degrees in a slanting position on the optical axis L2, and a fixing-light projection system for presenting a fixing light for the subject eye E to be fixed is disposed on the optical axis along the reflecting direction.

A lens 23, a pinhole plate 24, and a photo-detector 25 are placed on an optical axis L3 along the reflection of the dichroic mirror 16. The objective lenses 10 and 11, the dichroic mirror 16, the lens 23, the pinhole plate 24, and the photo-detector 25 make up a corneal deformation detection system for detecting a change in the amount of corneal reflection light.

A piston 28 which is pushed up by the driving of a solenoid 27 is slidably fitted in a cylinder 26 inside the fluid chamber 13. The nozzle 12, the fluid chamber 13, the solenoid 27, and the piston 28 make up a pressure section. The fluid chamber 13 has a pressure sensor 29 for monitoring the pressure in the fluid chamber 13.

The output from the image-pickup element 19 is connected to a controller 31, to which an operating section 32, a monitor 33, the solenoid 27, and the LED light source 21 are connected. Furthermore, the measuring section accommodating the optical system of FIG. 1 is placed on a stage (not shown) and is driven by a motor in three axial directions, a direction along the optical axis L1 toward the subject eye E and directions perpendicular to the axis L1.

When an operator pushes a measurement start switch of the operating section 32, illuminating light flux from the external eye-illuminating light sources 20a and 20b illuminates the anterior ocular segment of the subject eye E. The illuminating light flux reflected and diverged by the anterior ocular segment is substantially collimated by the objective lenses 10 and 11, passes through the observing window 14 and the dichroic mirrors 15 and 16, then passes through the aperture in the center of the prism diaphragm 17, and is imaged on the image-pickup element 19 through the imaging lens 18.

The controller 31 performs rough alignment such that it senses a pupil to find the center of the pupil by binarizing the anterior ocular segment image obtained from the image-pickup element 19 with an appropriate threshold, and when the relative position between the optical axis L1 of the measuring section and the pupil of the subject eye E in the plane in the direction of x, y perpendicular to the optical axis L1 is not in a permissible range, the stage is driven to move the measuring section so as to be within the permissible range.

When the positioning of the subject eye E and the measuring section in the plane perpendicular to the optical axis L1 has been substantially finished, the controller 31 turns on the LED light source 21. The light flux from the LED light source 21 is once imaged in the nozzle 12 through the projection lens 22 and the dichroic mirror 15, reaches the subject eye E, and is reflected by the cornea Ec. The light flux reflected by the cornea EC is collected by the objective lenses 10 and 11, passes through the observing window 14, and thereafter, substantially 50 percent passes through the dichroic mirror 15 and part of that 50 percent passes through the dichroic mirror 16.

The light flux that has passed through the dichroic mirror 16 is split into three pencils of light through the three apertures of the prism diaphragm 17 and is imaged on the image-pickup element 19 through the imaging lens 18. At that time, the pencils of light that have passed through the upper and lower apertures of the prism diaphragm 17 are polarized into and out of the plane of the paper by the polarizing prisms 17a and 17b, respectively, so that the positional relationship among the three-split bright point images of the cornea from the LED light source 21 varies depending on the relative position between the subject eye E and the measuring section. The determination of the positional relationship among the three-split corneal bright point images allows the positional relationship between the subject eye E and the measuring section to be found.

For example, when the distance between the subject eye E and the measuring section is longer than a predetermined distance, a corneal bright-point image into the plane of the paper on the image-pickup element 19 is moved downward and an image on this side is moved upward. On the other hand, when the distance between the subject eye E and the measuring section is shorter than the predetermined distance, the corneal bright-point image into the plane of the paper on the image-pickup element 19 is moved upward and the image on this side is moved downward. When the positions of the subject eye E and the measuring section in the plane perpendicular to the optical axis L1 deviate from each other, the positional relationship between the subject eye E and the measuring section can be found by sensing the gravity of the three corneal bright-point images or the position of the central corneal bright-point image.

The controller 31 performs close alignment such that it drives the stage so that the positional relationship between the subject eye E and the measuring section is within a predetermined range. When the positioning between the subject eye E and the measuring section has been finished, the controller 31 drives the solenoid 27 to move the piston 28. Then the pressure in the fluid chamber 13 increases. The pressure is sensed by the pressure sensor 29 and at the same time, a fluid-flow, for example airflow, having a strength with an increasing pressure within the fluid chamber 13 is blown from the nozzle 12 to the cornea Ec of the subject eye E. The cornea Ec starts to be deformed depending on the strength of the fluid-flow.

In the corneal deformation detection system, when the curvature radius R of the cornea has become a predetermined curvature radius Ra by the fluid-flow in pulse form, the photo-detector 25 detects a virtual image formed by the reflection of the light flux by the cornea Ec, the light flux being emitted from the LED light source 21 and projected on the cornea Ec, and light flux that has passed through pinholes in the pinhole plate 24. The pinhole plate 24 is arranged in the position optically conjugate with the objective lenses 10 and 11 and the lens 23. In the noncontact tonometer according to the first embodiment, the amount of light received by the photo-detector 25 increases as the curvature radius R of the cornea Ec comes close to the predetermined curvature radius Ra, which becomes a peak value at which the curvature radius Ra is infinite. In other words, the noncontact tonometer detects a peak value when the cornea Ec becomes flat by the compressed air in pulse form.

Accordingly, by obtaining the value of an output signal from the pressure sensor 29 when an output signal from the photo-detector 25 in the corneal deformation detection system has reached its peak value, a pressure necessary to deform the curvature radius R of the cornea Ec into Ra can be given, and so the intraocular pressure P of the subject eye E can be given by converting the value.

Figure 3B:
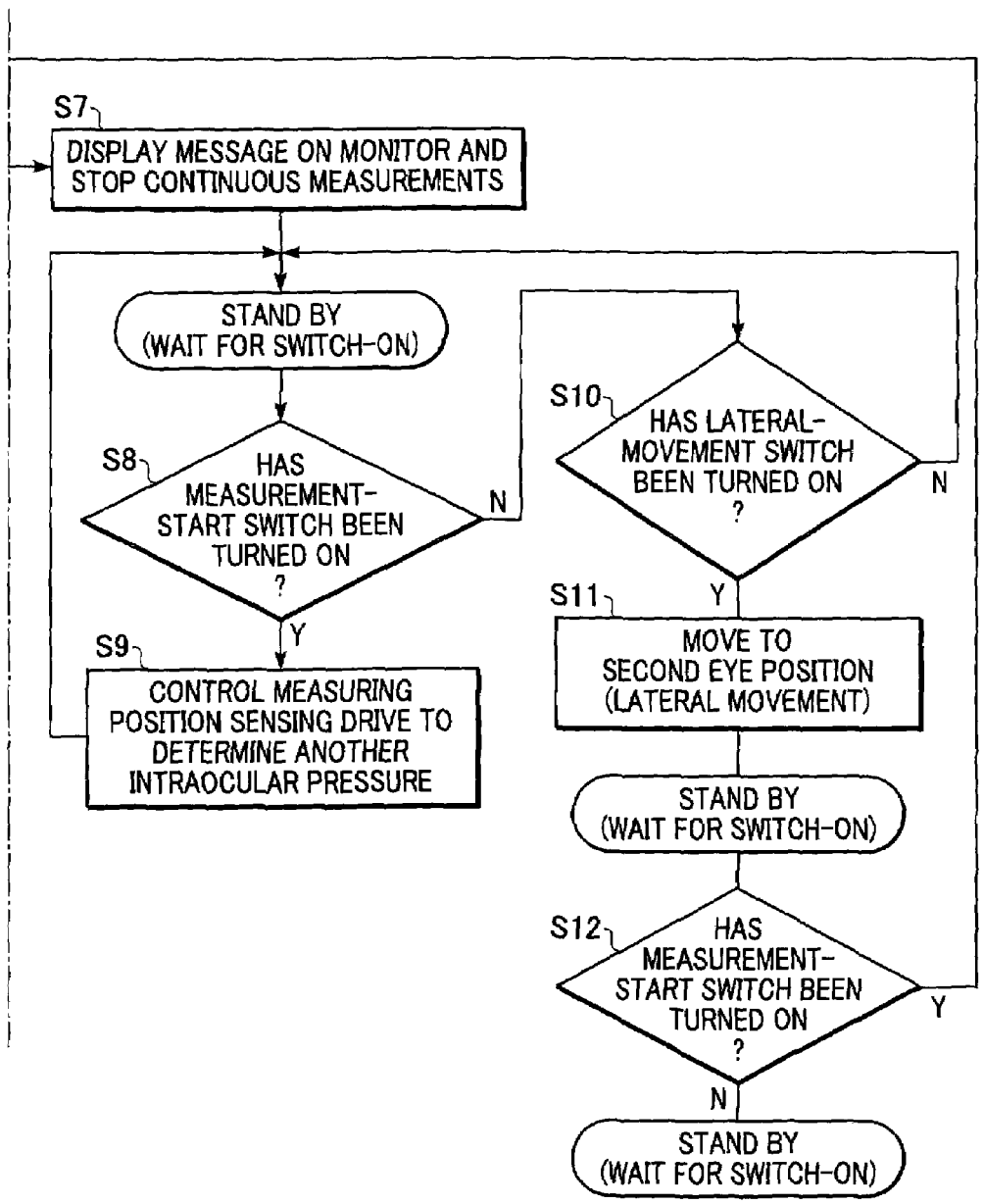
FIG. 3 is a flowchart for the control operation of the first embodiment.

FIG. 3 is a flowchart for the control operation of the first embodiment; in step 1, intraocular pressure measurement is performed by the rough alignment by the pupil-position sensing, the close alignment by the corneal bright-point detection, the driving of the solenoid 27, and the corneal deformation detection.

In step 2, it is determined by the controller 31 whether a predetermined number n of intraocular pressure measurements have been finished. When measured intraocular pressures include n values, from P1 to Pn, the process proceeds to step S3. When they are less than n, the process returns to step S1, wherein the alignments and the intraocular pressure measurement are performed again.

Figure 4:
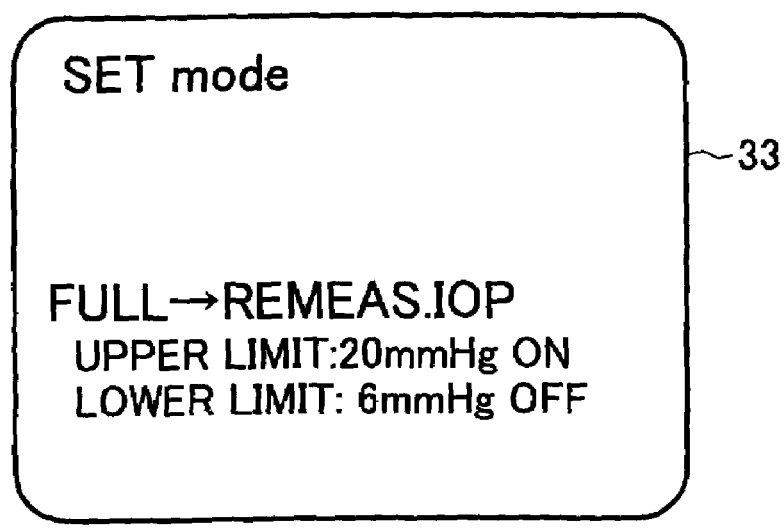
FIG. 4 is an explanatory diagram of a setting screen of a monitor.

FIG. 4 shows a setting screen displayed on the monitor 33. The first embodiment can set two values in advance by the controller 31, as shown in FIG. 4. Referring to FIG. 4, "UPPER LIMIT: 20 mmHg ON" indicates an upper limit PH at which a series of measuring operations is changed when a measured intraocular pressure P has exceeded 20 mmHg. "LOWER LIMIT: 6 mmHg OFF" indicates a lower limit PL at which a series of measuring operations is changed when the measured intraocular pressure P has fallen below 6 mmHg, wherein the indication is "OFF," so that the lower limit PL is set invalid.

The set values of the upper limit PH and the lower limit PL can be arbitrarily varied, and also whether they are set valid or invalid can be arbitrarily set.

In step S3, the controller 31 compares the respective n intraocular pressure values P1 through Pn measured n times with the upper limit PH to determine whether or not at least one intraocular pressure value P exceeding the upper limit PH exists. When no intraocular pressure value P exceeding the upper limit PH exists, the process proceeds to step S4. In the first embodiment, since the lower value PL is set to invalid, the process passes through the step S4 to step S5.

In step S5, it is determined whether or not the measurements of left and right intraocular pressures have been finished. When the measurement of both the left and right intraocular pressures has been completed, the controller 31 completes the measuring operation. When the measurement of both the left and right intraocular pressures has not been completed, the process proceeds to step S6, wherein the controller 31 drives the stage to move the measuring section to the other eye that has not yet been examined.

When the lateral movement has been accomplished, the process returns to step S1, wherein the controller 31 performs intraocular-pressure measurement for the eye that has not yet been examined. The measurement is accomplished by the rough alignment by the pupil-position sensing, the close alignment by the corneal bright-point detection, the driving of the solenoid 27, and the corneal deformation detection. Thereafter, the process proceeds to steps S2 through S5, wherein when the intraocular pressures of both eyes have been measured, the measuring operation is completed.

On the other hand, in step S3, the controller 31 compares the respective n intraocular pressure values P1 through Pn measured n times with the upper limit PH to determine whether or not at least one intraocular pressure value P exceeding the upper limit PH exists. When at least one intraocular pressure value P exceeding the upper limit PH exists, the process of the controller 31 proceeds to step S7.

Figure 5:
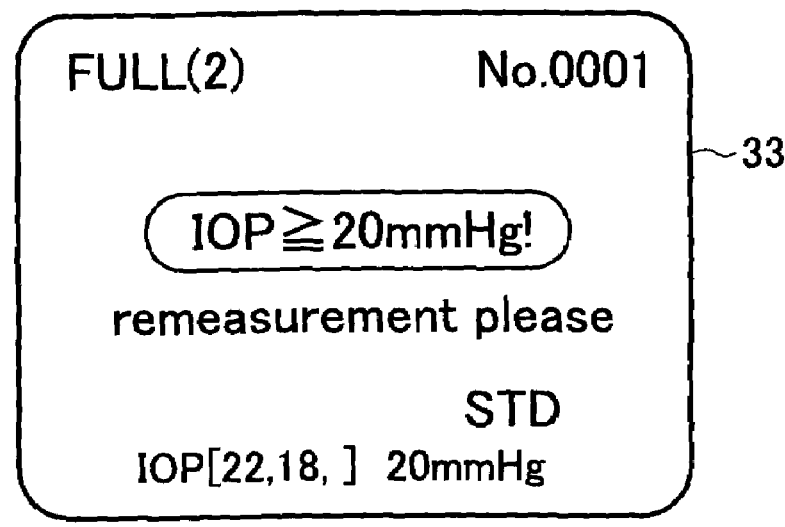
FIG. 5 is an explanatory diagram of an intraocular pressure and a message on the monitor.

FIG. 5 is an explanatory diagram of the screen of the monitor 33 on which an intraocular pressure is displayed. The screen also displays a message when the designated number n of measurements =2. When it has been determined in step S3 that at least one intraocular pressure value P exceeding the upper limit PH exists, the controller 31 displays n intraocular pressures P1 through Pn and a message M on the monitor 33 to notify the operator that an intraocular pressure value P exceeding the upper limit PH exists and to recommend additional measurement for confirmation, and then stops the continuous measuring operations. The controller 31 then goes into an input standby mode for operation switches of the operating section 32.

During the input standby mode, when the operator determines that an additional intraocular-pressure measurement is necessary and pushes a measurement start switch of the operating section 32, the process of the controller 31 proceeds to step S9. In step S9, the same control as that in step S1 is performed, wherein intraocular pressure measurement is performed by the rough alignment by the pupil-position sensing, the close alignment by the corneal bright-point detection, the driving of the solenoid 27, and the corneal deformation detection.

When the additional intraocular-pressure measurement has been finished, the controller 31 again goes into the input standby mode for operation switches of the operating section 32. On the other hand, when the operator determines that the additional intraocular-pressure measurement is not necessary and pushes an R/L movement switch of the operating section 32, the process of the controller 31 proceeds to step S10.

In step S10, the controller 31 drives the stage to move the measuring section laterally to the other eye position and comes into standby mode for inputting the operation switches of the operating section 32. When the operator pushes the measurement start switch of the operating section 32, the process of the controller 31 returns to step S1, wherein the series of measuring operations from step S1 through step S5 are performed again.

With the noncontact tonometer for performing a designated number of measurements by the series of measuring operations according to the first embodiment, as described above, the upper limit PH and the lower limit PL are set, the obtained intraocular pressure P is compared with the upper limit PH or the lower limit PL, and when the obtained intraocular pressure P is higher than the upper limit PH or lower than the lower limit PL, the series of measuring operations is stopped. The termination of measuring operations is indicated on a display device such as the monitor 33 to notify the operator, thereby recommending additional measurement. Accordingly, there is no need to move the measuring section into the measuring position again after completion of the measurements of both eyes. Thus, the efficiency of additional measurement is increased and the operator is prevented from forgetting additional measurement for confirmation.

According to the first embodiment, when it has been determined that the obtained intraocular pressure P is abnormal, the operator is notified of that by an indication on the display device such as the monitor 33; however, the operator can be notified by sound or a beeper, thus offering similar effects.

Furthermore, according to the first embodiment, after the predetermined number n of intraocular-pressure measurements have been completed, the measurements are compared with the upper limit PH or the lower limit PL. However, it is also possible to compare the intraocular pressure P with the upper limit PH or the lower limit PL for each measurement, wherein, when the intraocular pressure P is abnormal, the series of measuring operations is terminated and the message M is displayed on the monitor 33 to notify the operator of it.

Second Embodiment

Figure 6:
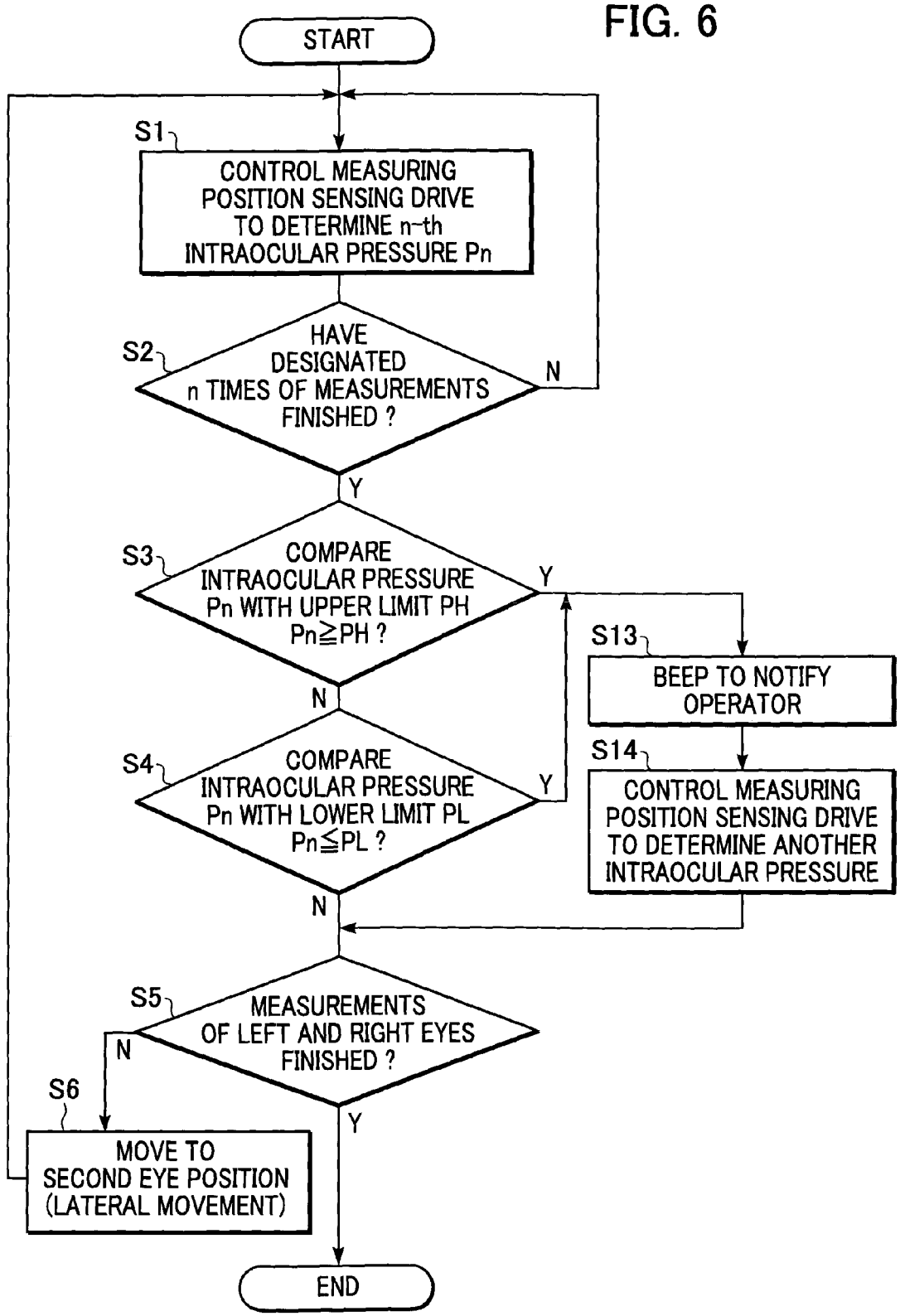
FIG. 6 is a flowchart for the control operation of a second embodiment.

FIG. 6 is a flowchart for the control operation of a second embodiment. Steps S1 to S6 are the same as those of FIG. 3A. When the operator pushes the measurement start switch of the operating section 32 of FIG. 1, intraocular pressure is measured by the controller 31 in step S1 by the rough alignment by the pupil position sensing, the close alignment by the corneal bright point detection, the driving of the solenoid 27, and the corneal deformation detection. In step S2, it is determined whether or not the predetermined number n of intraocular-pressure measurements has been finished. When the number n of intraocular-pressure measurements has been completed, the process proceeds to step S3, and when the number of times is less than n, the process returns to step S1, wherein the alignment and the intraocular-pressure measurement are performed again.

Two values of the upper limit PH and the lower limit PL can be set in advance, as in the first embodiment. The upper limit PH and the lower limit PL can be arbitrarily varied and whether they are set valid or invalid can be arbitrarily set.

Subsequently in step S3, the controller 31 compares the respective n intraocular pressure values, P1 through Pn measured n times with the upper limit PH to determine whether or not at least one intraocular pressure value P exceeding the upper limit PH exists. When no intraocular pressure value P exceeding the upper limit PH exists, the process proceeds to step S4. Also in the second embodiment, when the lower value PL is set to invalid, the process passes through the step S4 to step S5.

In step S5, it is determined whether or not the measurements of the left and right intraocular pressures have been accomplished. When the measurements of left and right intraocular pressures have been completed, the controller 31 completes the measuring operation. When the measurements of left and right intraocular pressures have not been accomplished, the process proceeds to step S6, wherein the controller 31 drives the stage to move the measuring section to the other eye that has not been examined.

When the lateral movement has been completed, the process returns to step S1, wherein the controller 31 performs intraocular-pressure measurement for the other subject eye that has not yet been examined, by the rough alignment by the pupil-position sensing, the close alignment by the corneal bright-point detection, the driving of the solenoid 27, and the corneal deformation detection. Thereafter, the process proceeds to steps S2 through S5, wherein when the intraocular pressures of both eyes have been measured, the measuring operation is completed.

In step S3, when it has been determined that at least one intraocular pressure value P exceeding the upper limit PH exists, the controller 31 displays n intraocular pressures P1 through Pn on the monitor 33 and sounds a beeper to notify the operator that an intraocular pressure value P exceeding the upper limit PH exists at step S13, and the process proceeds to step S14.

In step S14, although the designated number n of measurements has been finished, a predetermined additional number m of intraocular-pressure measurements is automatically performed by the rough alignment by the pupil-position sensing, the close alignment by the corneal bright-point detection, the driving of the solenoid 27, and the corneal deformation detection. When the automatic additional number m of intraocular-pressure measurements has been finished, the process proceeds to step S5, and subsequently the series of measuring operations is performed as described above.

With the noncontact tonometer for performing a designated number of measurements by a series of measuring operations according to the second embodiment, as described above, the upper limit PH and the lower limit PL are set, the obtained intraocular pressure P is compared with the upper limit PH or the lower limit PL, and when the obtained intraocular pressure P is higher than the upper limit PH or lower than the lower limit PL, the operator is notified by a beeper.

The predetermined number m of additional intraocular-pressure measurements is automatically performed and the measuring section is moved to the eye position that has not yet been examined, where the predetermined number n of intraocular-pressure measurements is performed, thus increasing the efficiency of the additional measurements. Also, there is no need for the operator to perform additional measurements for confirmation, thus preventing the problem of the operator's forgetting to perform additional measurements.

According to the second embodiment, it is also possible to set the upper limit PH and the lower limit PL, and to compare the obtained intraocular pressure P with the upper limit PH or the lower limit PL. When the obtained intraocular pressure P is higher than the upper limit PH, the solenoid 27 can be controlled to blow fluid with a force that is stronger than normal onto the cornea Ec, and when the intraocular pressure P is lower than the lower limit PL, the solenoid 27 can be controlled to blow fluid with a weaker force onto the cornea Ec.

In this way, for the subject eye E having an intraocular pressure P higher than the higher limit PH, the accuracy of measurement is improved, and for the subject eye E having an intraocular pressure P lower than the lower limit PL, there is no need to blow fluid more than necessary onto the subject eye E, thus reducing the load on the subject.

In the noncontact tonometer according to embodiments of the present invention, even when predetermined times of intraocular-pressure measurements are performed by a series of measuring operations, the upper limit and the lower limit are set, and an obtained intraocular pressure is compared with the upper limit or the lower limit, and when the obtained intraocular pressure is higher than the higher limit or lower than the lower limit, the series of measuring operations is stopped and that is displayed on a display device such as a monitor to notify the operator, thus recommending additional measurement. Accordingly, there is no need to move a measuring section to the measuring position again after the completion of the measurement of both eyes, thus increasing the efficiency of additional measurement. Also the operator is prevented from forgetting to perform additional measurements for confirmation.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A noncontact tonometer comprising:
   fluid blowing means for blowing fluid onto a cornea to deform the cornea;
   measuring-light projecting means for projecting measuring light onto the cornea;
   corneal deformation detecting means for detecting the measuring light reflected by the cornea when the cornea is deformed by the fluid so as to have a predetermined curvature radius;
   calculating means for calculating intraocular pressure on the basis of the detection by the corneal deformation detecting means;

control means for controlling measuring operations of the noncontact tonometer performed sequentially a predetermined number of times; and comparing means for comparing the intraocular pressure obtained by the calculating means for each of the predetermined times with a predetermined limit, wherein the control means gives a warning if the intraocular pressure obtained by the calculating means for at least one of the predetermined number of times exceeds the predetermined limit.

2. A noncontact tonometer according to claim 1, wherein the control means adds a predetermined number of measurements depending on the comparison by the comparing means.

3. A noncontact tonometer according to claim 1, wherein the control means comprises notifying means for notifying an operator of the comparison by the comparing means.

4. A noncontact tonometer according to claim 1, wherein the fluid blowing means comprises fluid control means for controlling the force of the fluid blown onto the cornea for varying the force of the blown fluid depending on the comparison by the comparing means.

5. A noncontact tonometer according to claim 1, wherein the measuring operation utilizes pupil-position sensing means for alignment, corneal bright-point detection means for close alignment, a solenoid for driving, and the corneal deformation detecting means.

6. A noncontact tonometer according to claim 1, wherein the measuring operation utilizes pupil-position sensing means for alignment, corneal bright-point detection means for close alignment, a solenoid for driving, the corneal deformation detecting means, and notifying means for notifying the operator of the comparison by the comparing means.

7. A noncontact tonometer comprising:

fluid blowing means for blowing fluid onto a cornea to deform the cornea;

measuring-light projecting means for projecting measuring light onto the cornea;

corneal deformation detecting means for detecting the measuring light reflected by the cornea when the cornea is deformed by the fluid so as to have a predetermined curvature radius;

calculating means for calculating intraocular pressure on the basis of the detection by the corneal deformation detecting means;

control means for controlling measuring operations of the noncontact tonometer so as to measure right and left eyes sequentially a predetermined number of times, respectively; and comparing means for comparing the intraocular pressure obtained by the calculating means for each of the predetermined number of times with a predetermined limit, wherein the control means stops the measuring operations after completion of the predetermined number of measurements of the eyes under measurement if the intraocular pressure obtained by the calculating means for at least one of the predetermined number of measurements exceeds the predetermined limit.

8. A noncontact tonometer comprising:

a measuring unit adapted to measure an intraocular pressure of a first eye; and a control unit for controlling a movement of the measuring unit to sequentially measure an intraocular pressure of a second eye after measuring the intraocular pressure of the first eye;

wherein the control unit terminates a measuring operation without causing the measuring unit to move to measure the intraocular pressure of the second eye if the measured intraocular pressure of the first eye exceeds a predetermined limit.

9. The noncontact tonometer according to claim 8, wherein the measuring unit includes;

a fluid blowing unit adapted to blow fluid onto a cornea to deform the cornea;

a measuring-light projecting unit adapted to project measuring light onto the cornea; and a corneal deformation detecting unit adapted to detect the measuring light reflected by the cornea deformed by the fluid.

10. The noncontact tonometer according to claim 8, wherein the control unit controls a display of a message if the measured intraocular pressure of the first eye exceeds the predetermined limit.

11. The noncontact tonometer according to claim 8, wherein the control unit controls the measuring unit to additionally measure an intraocular pressure in response to activation of a measurement start switch, if the measured intraocular pressure of the first eye exceeds the predetermined limit.

12. The noncontact tonometer according to claim 8, wherein the control unit controls the movement of the measuring unit in response to activation of a movement switch, if the measured intraocular pressure of the first eye exceeds the predetermined limit.

* * * * *

UNITED STATES PATENT AND TRADEMARK OFFICE
CERTIFICATE OF CORRECTION

PATENT NO.        : 7,235,051 B2
APPLICATION NO.   : 10/645480
DATED             : June 26, 2007
INVENTOR(S)       : Tomoyuki Iwanaga Page 1 of 1

It is certified that error appears in the above-identified patent and that said Letters Patent is hereby corrected as shown below:

COLUMN 3:
Line 50, "cornea EC" should read --cornea Ec--.

COLUMN 10:
Line 17, "eye;" should read --eye,--.
Line 24, "includes;" should read --include:--.

Signed and Sealed this

Eleventh Day of March, 2008

JON W. DUDAS
*Director of the United States Patent and Trademark Office*